(12) United States Patent
Li et al.

(10) Patent No.: US 11,473,019 B2
(45) Date of Patent: Oct. 18, 2022

(54) NAPHTHA CATALYTIC CRACKING CATALYST, CATALYTIC CRACKING METHOD AND REACTION DEVICE

(71) Applicants: SHANGHAI SUPEZET ENGINEERING TECHNOLOGY CO., LTD., Shanghai (CN); JIANGSU BOSONG CHEMICAL TECHNOLOGY CO., LTD., Jiangsu (CN); HANYI SHENFEI NEW MATERIALS CO., LTD., Henan (CN); CHINA UNIVERSITY OF PETROLEUM (EAST CHINA), Shandong (CN)

(72) Inventors: Chunyi Li, Shandong (CN); Lingyun Zhang, Henan (CN); Xiaoyu Zhang, Shanghai (CN); Ying Zhang, Shanghai (CN); Kaitian Mao, Shanghai (CN); Hui Li, Shanghai (CN); Chuntian Pang, Jiangsu (CN)

(73) Assignees: SHANGHAI SUPEZET ENGINEERING TECHNOLOGY CO., LTD., Shanghai (CN); JIANGSU BOSONG CHEMICAL TECHNOLOGY CO., LTD., Jiangsu (CN); HANYI SHENFEI NEW MATERIALS CO., LTD., Henan (CN); CHINA UNIVERSITY OF PETROLEUM (EAST CHINA), Shandong (CN)

(*) Notice: Subject to any disclaimer, the term of this patent is extended or adjusted under 35 U.S.C. 154(b) by 0 days.

(21) Appl. No.: 17/279,856

(22) PCT Filed: Sep. 19, 2019

(86) PCT No.: PCT/CN2019/106752
§ 371 (c)(1),
(2) Date: Mar. 25, 2021

(87) PCT Pub. No.: WO2020/063449
PCT Pub. Date: Apr. 2, 2020

(65) Prior Publication Data
US 2022/0033713 A1   Feb. 3, 2022

(30) Foreign Application Priority Data

Sep. 27, 2018 (CN) .......................... 201811135535.4
Mar. 18, 2019 (CN) ......................... 201910201901.X
Apr. 3, 2019 (CN) .......................... 201910265854.5

(51) Int. Cl.
*C10G 11/18* (2006.01)
*B01J 8/18* (2006.01)
(Continued)

(52) U.S. Cl.
CPC ............. *C10G 11/18* (2013.01); *B01J 8/0055* (2013.01); *B01J 8/1827* (2013.01); *B01J 8/1845* (2013.01);
(Continued)

(58) Field of Classification Search
CPC ....................... B01J 21/02; B01J 2208/00902; B01J 23/755; B01J 8/0055; B01J 8/0065;
(Continued)

(56) References Cited

U.S. PATENT DOCUMENTS 3,725,495 A   4/1973   Wrisberg et al.
4,664,888 A   5/1987   Castagnos, Jr.
(Continued)

FOREIGN PATENT DOCUMENTS

CN   1165052 A   11/1997
CN   1319643 A   10/2001
(Continued)

OTHER PUBLICATIONS

CN101116827A—English Translation—Google Patents (Year: 2008).*
(Continued)

*Primary Examiner* — Ellen M McAvoy
*Assistant Examiner* — Chantel L Graham
(74) *Attorney, Agent, or Firm* — Buchanan Ingersoll & Rooney PC (57) ABSTRACT

A method for catalytic cracking of naphtha is provided. Naphtha is catalytically cracked under the action of a catalyst. The catalyst includes aluminosilicate, alkali metal oxide, alkaline earth metal oxide, $TiO_2$, iron oxide, vanadium oxide and nickel oxide. On the other hand, a rapid
(Continued)

separation component is arranged in a disengager of a catalytic cracking reaction device, so that a transport disengaging height is greatly reduced without changing a gas flow and a diameter of the disengager. In addition, the separation efficiency of oil gas and the catalyst is improved.

19 Claims, 7 Drawing Sheets

(51) Int. Cl.
  *B01J 8/38* (2006.01)
  *B01J 8/00* (2006.01)
  *B01J 21/02* (2006.01)
  *B01J 23/755* (2006.01)
(52) U.S. Cl.
  CPC .............. *B01J 8/388* (2013.01); *B01J 21/02* (2013.01); *B01J 23/755* (2013.01); *B01J 2208/00902* (2013.01); *C10G 2300/1044* (2013.01); *C10G 2300/70* (2013.01); *C10G 2400/20* (2013.01)
(58) Field of Classification Search
  CPC ...... B01J 8/1827; B01J 8/1845; B01J 8/1863; B01J 8/26; B01J 8/388; C07C 4/06; C10G 11/18; C10G 2300/1044; C10G 2300/70; C10G 2400/20
  See application file for complete search history.

(56) References Cited

U.S. PATENT DOCUMENTS

| | | | |
|---|---|---|---|
| 4,793,915 | A | 12/1988 | Haddad et al. |
| 4,816,137 | A | 3/1989 | Swint et al. |
| 5,348,644 | A | 9/1994 | Maroy et al. |
| 2016/0101396 | A1 | 4/2016 | Xu et al. |
| 2018/0280909 | A1 | 10/2018 | Li et al. |

FOREIGN PATENT DOCUMENTS

| | | | | | |
|---|---|---|---|---|---|
| CN | 2489874 | Y | | 5/2002 | |
| CN | 101116827 | A | * | 2/2008 | .............. C07C 4/06 |
| CN | 101116827 | A | | 2/2008 | |
| CN | 101164684 | A | | 4/2008 | |
| CN | 102234531 | A | | 11/2011 | |
| CN | 102463072 | A | | 5/2012 | |
| CN | 104388112 | A | | 3/2015 | |
| CN | 104419458 | A | | 3/2015 | |
| CN | 105349178 | A | | 2/2016 | |
| CN | 105368483 | A | | 3/2016 | |
| CN | 206298550 | U | | 7/2017 | |
| CN | 107974285 | A | * | 5/2018 | |
| CN | 107974285 | A | | 5/2018 | |
| CN | 207463192 | U | | 6/2018 | |
| CN | 109232153 | A | | 1/2019 | |
| CN | 109499486 | A | | 3/2019 | |
| GB | 897796 | A | | 5/1962 | |
| WO | 2013054173 | A1 | | 4/2013 | |
| WO | 2014/209653 | A1 | | 12/2014 | |

OTHER PUBLICATIONS

CN107974285A—English Translation—Google Patents (Year: 2018).*
CN107974285A—English Translation—Description (Year: 2018).*
International Search Report and Written Opinion dated Dec. 18, 2019, by the China National Intellectual Property Administration as the International Searching Authority for International Application No. PCT/CN2019/106752.
Wang et al., "Numerical Simulation of the Influence of Injecting Velocity and Angle of Flow and Reaction in RFCC Riser Reactor," Journal of Chemical Industry and Engineering (China), Apr. 1999, vol. 50, No. 2, pp. 200-207, and an English translation of the abstract. (8 pages).
Wu et al., "Study on Characteristics of Gas-Solids Flow in Diameter-Enlarged Section of a Novel Riser Reactor," Petroleum Processing and Petrochemicals, Nov. 2014, vol. 45, No. 11, pp. 54-59, and an English translation of the abstract. (6 pages).

* cited by examiner

NAPHTHA CATALYTIC CRACKING CATALYST, CATALYTIC CRACKING METHOD AND REACTION DEVICE

TECHNICAL FIELD

The present application relates to the field of petrochemical industry, in particular to a method and device for catalytic cracking of alkanes.

BACKGROUND

Steam cracking of hydrocarbons has always been the mainstream production technology for low-carbon olefins such as ethylene and propylene. Materials for steam cracking mainly include ethane, propane, butane, straight-run naphtha and other light hydrocarbons. In theory, heavy hydrocarbons, except arene, can also be used as materials for steam cracking, but when heavy hydrocarbons undergo steam cracking, the coking of a cracking furnace will be more serious. In addition, the content of olefins in the materials for steam cracking needs to be strictly limited. A high content of olefins may also accelerate the coking of cracking furnace tubes. The amount of water vapor used in steam cracking is relatively large, and the steam/hydrocarbon mass ratio is generally about 0.5. In addition, the reaction temperature of steam cracking is relatively high, generally 800° C. or higher. The high temperature and large amount of water vapor lead to very high energy consumption in the reaction.

Steam cracking is a thermal reaction. For many years, researchers have hoped to reduce the reaction temperature and the amount of water vapor by means of catalytic reactions. From the public reports in the literature, researchers have proposed a variety of solutions no matter for catalysts or reactors, for example, a method of combining steam cracking and catalytic cracking, or modifications to a catalytic cracking method.

The present application aims to broaden catalytic cracking reaction methods of alkanes.

SUMMARY

In one aspect, a first objective of the present application is to provide a catalyst for a catalytic cracking of naphtha, which has high catalytic efficiency.

The catalyst for a catalytic cracking of naphtha includes aluminosilicate, alkali metal oxide, alkaline earth metal oxide, $TiO_2$, iron oxide, vanadium oxide and nickel oxide.

The catalyst is used for catalytic cracking of alkanes, especially for a catalytic cracking reaction of naphtha, and has a catalytic effect.

In another aspect, a second objective of the present application is to provide a method for a catalytic cracking of naphtha. In the method, the reaction temperature of the catalytic cracking is significantly lower than the reaction temperature in the traditional steam cracking method.

The method for the catalytic cracking of naphtha includes the following step:

naphtha undergoes catalytic cracking reaction under the action of the above catalyst.

The temperature of the naphtha catalytic cracking under the above conditions can be lowered by about 100° C. compared with the traditional cracking method.

A third objective of the present application is to provide a method for the catalytic cracking of naphtha, which can reduce or avoid coking in a reaction section.

The method for catalytic cracking of naphtha includes the following steps:

S1: the catalyst enters a pre-lift pipe through a regenerator sloped pipe and flows upward into a dense phase section of the reactor under the action of a pre-lift medium, and a feedstock is sprayed into a reactor tangentially upward through a nozzle located at a bottom of the dense phase section of the reactor;

the nozzle of the reactor sprays the feedstock along a tangential direction of a cross-sectional circular ring and at an angle of 10-90° to a vertical direction;

S2: oil gas and the catalyst leaving a riser pipe enter a disengager of a reaction device, the oil gas leaves the disengager to enter a separation system, and the catalyst flows out through a conveying part of a cyclone and falls into a stripping section of a disengager;

S3: the catalyst is stripped, then the stripped catalyst enters a regenerator through a spent sloped pipe, and the catalyst is heated in the regenerator; and S4: the heated catalyst enters a disengager section of the regenerator, falls into a stripping section of the disengager section of the regenerator and then enters a degassing tank, and the catalyst is further stripped in the degassing tank and the stripped catalyst returns to the reactor through the regenerator sloped pipe.

Through the arrangement manner of the feed nozzle in the reactor, the catalyst can be driven to rotate to reduce a stagnant zone in the dense phase section, thereby reducing or avoiding coking in the reactor.

A fourth objective of the present application is to provide a catalyst regeneration device. The gas-solid separation effect in a disengager of the regeneration device is high, and the loss of the catalyst is reduced.

The catalyst regeneration device of the present application includes a reaction section of the regenerator and a disengager section of the regenerator. The disengager section of the regenerator is located above the reaction section of the regenerator, an outlet of the reaction section of the regenerator is located inside the disengager section of the regenerator; and a primary cyclone, a raising pipe of the primary cyclone and a cover are arranged in the disengager section of the regenerator. The cover includes an upper part and a lower part, the upper part of the cover is in a shape of a truncated cone, a lower base of the truncated cone is the lower part of the cover, and the lower part of the cover is in a cylindrical structure. An area of an opening in a lowermost end of the cover is greater than an area of an outlet of the reactor. An outer circumference of an upper base of the truncated cone is connected with a periphery of the raising pipe of the primary cyclone, or the outer circumference of the upper base of the truncated cone is connected with a periphery of the primary cyclone above its inlet.

In another aspect, the catalyst regeneration device of the present application includes a reaction section of the regenerator and a disengager section of the regenerator. The disengager section of the regenerator is communicated with the reaction section of the regenerator, an outlet of the reaction section of the regenerator is located inside the disengager section of the regenerator, a first splitter and a second splitter are arranged in the disengager section of the regenerator, and the first splitter and the second splitter are both located above the outlet of the reaction section. The first splitter is a component that reduces gas velocity in the upward direction of a gas flow discharged from the outlet of the reactor, the second splitter includes a second cover whose cross-sectional area gradually decreases from bottom to top, the second cover is provided with openings at both uppermost end and lowermost end, and the first splitter is located in the second splitter.

In the catalyst regeneration device of the present application, a transport disengaging height is greatly reduced without changing a gas flow and a diameter of the disengager section of the regenerator. In addition, a separation efficiency of flue gas and the catalyst is improved.

DETAILED DESCRIPTION

In order to better understand the content of the present application, the technical solutions of the present application will be described clearly and completely in conjunction with specific embodiments, examples and accompanying drawings of the present application. The following embodiments are used to illustrate the present application, but not to limit the scope of the present application.

The experimental methods that do not indicate specific conditions in the following examples usually follow the conventional conditions or the conditions recommended by the manufacturer. Unless otherwise stated, all percentages, rates, ratios or parts are based on weight.

Dense phase section: this section has larger bed diameter, lower gas velocity and higher catalyst fluidization density, and is conducive to the contact and reaction between gas phase and solid phase.

Riser section: This section has smaller bed diameter, higher gas velocity and lower catalyst fluidization density. Purposes: the linear velocity is increased, so that oil gas or flue gas leaves the reactor quickly, thereby reducing secondary reactions of olefins; the low catalyst density also helps to reduce secondary reactions, especially generation of coke; and this section is needed by catalyst transport.

The "peripheral wall" of the reactor of the present application refers to a wall of the reactor parallel to a central axis of the reactor.

Cracking, also known as pyrolysis, refers to the process in which organic compounds are thermally decomposed and condensed to produce products with different relative molecular masses.

The term "mass spacetime" refers to a ratio of the mass of the catalyst to the mass of the feed per hour.

The term "superficial gas velocity" refers to the velocity at which fluid escapes from a bed material after the bed is fluidized, and is an important operating parameter of a circulating fluidized bed.

The term "angle of repose", also referred to as critical angle of repose, is a minimum angle between an inclined surface and a horizontal surface in the case that an object placed on the inclined surface is in a critical state of sliding down the inclined surface (that is, as the angle of inclination increases, the object on the inclined surface will slide down more easily; and when the object reaches the state of beginning to slide, the angle in the critical state is called the angle of repose).

The term "oil gas" refers to the sum of all reactants and products in a reaction device in the present application.

Unless otherwise defined, all professional and scientific terms used herein have the same meanings as those familiar to those skilled in the art. In addition, any methods and materials that are similar or equivalent to the disclosed content can be applied to the methods of the present application. The preferred implementation methods and materials described herein are for exemplary purposes only.

In one aspect, a catalyst for the catalytic cracking of naphtha of the present application includes aluminosilicate, alkali metal oxide, alkaline earth metal oxide, $TiO_2$, iron oxide, vanadium oxide and nickel oxide.

The aluminosilicate includes $SiO_2$ and $Al_2O_3$. The aluminosilicate is selected from one or more components from a group consisting of molecular sieve, kaolin and mullite. Or the aluminosilicate is composed of $SiO_2$ or silica sol (the precursor of Sift) and/or precursors of sodium silicate and $Al_2O_3$.

In an embodiment, mass percentages of components in the catalyst are:

the mass percentage of $SiO_2$ is 30~80 wt %, and the mass percentage of $Al_2O_3$ is 10~70 wt %.

In some embodiments, mass percentages of components in the catalyst are: the mass percentage of $SiO_2$ is 40-60 wt %, and the mass percentage of $Al_2O_3$ is 25-60 wt %.

In some embodiments, a mass percentage of the alkali metal oxide is not greater than 5 wt %, and preferably not greater than 3 wt %. The alkali metal oxide includes one or two of $Na_2O$ and $K_2O$.

In some embodiments, a mass percentage of the alkaline earth metal oxide is not greater than 5 wt %, and preferably not greater than 3 wt %. The alkaline earth metal oxide includes one or two of CaO and MgO.

In some embodiments, a mass percentage of the $TiO_2$, the iron oxide, the vanadium oxide and the nickel oxide is not greater than 2 wt %, and preferably not greater than 1 wt %.

In the p resent application, the oxides of subgroup metal elements in the catalyst may be one or a mixture of two or more than two of $TiO_2$, iron oxide, vanadium oxide and nickel oxide, and the mass percentage of all the oxides of subgroup metal elements is not greater than 2 wt %, preferably not greater than 1 wt %.

The catalyst for the catalytic cracking of the present application has good thermal and hydrothermal stability and suitable acidity. In another aspect, the catalyst of the present application has a specific surface area of not greater than 150 $m^2/g$, preferably not greater than 80 $m^2/g$, and has high mechanical strength.

The catalyst for catalytic cracking of the present application can be prepared by using existing methods in this field, such as a precipitation method, an impregnation method and a mixing method.

In another aspect, a method for the catalytic cracking of naphtha includes:

S1: a catalyst enters a pre-lift pipe through a regenerator sloped pipe and flows upward into a dense phase section of the reactor under the action of a pre-lift medium, and a feedstock is sprayed into a reactor tangentially upward through a nozzle located at a bottom of the dense phase section of the reactor;

the reactor nozzle sprays the feedstock along a tangential direction of a cross-sectional circular ring and at an angle of 10-90° to a vertical direction;

S2: oil gas and the catalyst leaving a riser pipe enter a disengager of a reaction device, the oil gas leaves the disengager to enter a separation system, and the catalyst flows out through a conveying part of a cyclone and falls into a stripping section of the disengager;

S3: the catalyst is stripped, the stripped catalyst enters a regenerator through a spent sloped pipe, and the catalyst is heated in the regenerator; and S4: the catalyst enters a disengager section of the regenerator, falls into the stripping section of the regenerator and enters a degassing tank, and the catalyst is further stripped in the degassing tank and the stripped catalyst returns to the reactor through the regenerator sloped pipe.

The catalyst in the naphtha catalytic cracking reaction uses the catalyst for catalytic cracking provided in the present application.

In some embodiments, the pre-lift medium is selected from one or more components from a group consisting of steam, ethane, propane, butane and naphtha.

In the method for catalytic cracking of naphtha of the present application, the high-temperature catalyst firstly enters the pre-lift pipe, contacts and reacts with the pre-lift medium in the pre-lift pipe, and then enters the dense phase section. In the process of the catalyst moving upward in the pre-lift pipe and entering the dense phase section, the temperature of the catalyst gradually decreases. In the dense phase section, the catalyst contacts and reacts with naphtha. The temperature of catalyst entering the dense phase section is lower than that entering the pre-lift pipe, and the catalyst can contact and react with different hydrocarbons at different stages to meet the requirements of reaction temperatures of different raw materials. An end product, i.e., low-carbon olefins, has high selectivity, so that the generation of methane and other low-added-value products can be effectively reduced.

Compared with the steam cracking, the catalytic cracking method of the present application has the advantages of lower reaction temperature and lower steam consumption, so the energy consumption is reduced.

In some embodiments, the pre-lift medium is steam and ethane. A mass ratio of the steam to ethane is in a range from 1/20 to 1/1, preferably in a range from 1/10 to 1/2.

In the embodiment, the high-temperature catalyst (for example, with a temperature of about 800° C.) reacts with ethane in the pre-lift pipe, and then enters the dense phase section. The temperature of the catalyst can be reduced (for example, to about 700° C.) to just meet the naphtha reaction temperature.

In the method for catalytic cracking of naphtha of the present application, a mass ratio of ethylene to propylene can be adjusted by changing the reaction temperature and reaction components.

In some embodiments, the feedstock includes naphtha and steam. A mass ratio of the steam to naphtha is in a range from 1/20 to 1/1, preferably in a range from 1/10 to 1/2.

In some embodiments, the pre-lift medium is selected from one or more components from a group consisting of ethane, propane, butane and naphtha. The feedstock includes naphtha and steam, and a mass ratio of the steam to the sum of hydrocarbons as the pre-lift medium and naphtha is in a range from 1/20 to 1/1, preferably in a range from 1/10 to 1/2.

In some embodiments, the pre-lift medium includes steam and hydrocarbons, and the hydrocarbons include one or more components from a group consisting of ethane, propane, butane and naphtha. The feedstock includes naphtha. A mass ratio of the steam to the sum of hydrocarbons as the pre-lift medium and naphtha is in a range from 1/20 to 1/1, preferably in a range from 1/10 to 1/2.

In some embodiments, an average gas velocity in the dense phase section is greater than 0.25 m/s, preferably greater than 1 m/s.

An average retention time of the oil gas in the dense phase section is not more than 4 s, and preferably is not more than 2 s.

In some embodiments, in step S2, an average gas velocity in the riser pipe is greater than 3 m/s, preferably greater than 7 m/s. An average retention time in the riser pipe is not more than 5 s, and preferably is not more than 3 s.

In some embodiments, a linear velocity of the feedstock at an outlet of the nozzle is greater than 5 m/s, preferably greater than 10 m/s.

When the nozzle sprays the feedstock along a tangential direction of a cross-sectional circular ring of the dense phase section and at an angle of 10-90° to a vertical direction and the linear velocity at the outlet is greater than 5 m/s, the catalyst can be driven to rotate in the dense phase section to enhance the mass transfer, heat transfer and reaction between the oil gas and the catalyst and thus reduce the stagnant section in the dense phase section, thereby reducing or avoiding coking in the reactor. The reaction device can operate safely and stably for a long period.

In a third aspect, a naphtha catalytic cracking reaction device includes:

a pre-lift pipe, a dense phase section of the reactor, a first end of the dense phase section communicated with the pre-lift pipe, a regenerator sloped pipe, communicated with an inner of the pre-lift pipe, a nozzle, located at a bottom of the dense phase section of the reactor, a riser pipe, communicated with a second end of the dense phase section of the reactor, a disengager disengager section, communicated with the riser pipe, a disengager stripping section, communicated with the disengager disengager section, a spent sloped pipe, communicated with the disengager stripping section, and a degassing tank, connected with the spent sloped pipe and a regenerator.

A cross-sectional diameter of the riser pipe is less than a cross-sectional diameter of the dense phase section of the reactor.

In a fourth aspect, a catalyst regeneration device includes a reaction section of the regenerator and a disengager section of the regenerator. The reaction section adopts any structure disclosed in the prior art. A part of the reaction section extends into the disengager section.

The disengager section of the regenerator is located above the reaction section of the regenerator, an outlet of the reaction section is located inside the disengager section. And a primary cyclone, a raising pipe of the primary cyclone and a cover are arranged in the disengager section. The cover includes an upper part and a lower part, the upper part of the cover is in the shape of a truncated cone, a lower base of the truncated cone is the lower part of the cover, and the lower part of the cover is in a cylindrical structure. An area of an opening at a lowermost end of the cover is greater than an area of an outlet of the reactor. A circumference of an upper base of the truncated cone is connected with a periphery of the raising pipe of the primary cyclone, or the circumference of the upper base of the truncated cone is connected with a periphery of the primary cyclone above its inlet.

The cross section of the cylindrical structure of the lower part of the cover perpendicular to the axial direction may be equal or unequal. That is, the lower part of the cover may be a cylindrical structure whose diameter gradually decreases from top to bottom, or a cylindrical structure whose diameter gradually increases from top to bottom. Preferably, the lower part of the cover is in a cylindrical structure with equal diameter.

The primary cyclone is in any structure disclosed in the prior art, and usually includes a primary cyclone body and a conveying part, and the conveying part is located below the primary cyclone body.

In an embodiment, an outlet of the conveying part of the primary cyclone is lower than the outlet of the reactor.

In an embodiment, an angle θ between the generatrix of the truncated cone and the lower base of the truncated cone of a truncated cone-shaped part of the cover is greater than an angle of repose of catalyst granules, thereby ensuring that the catalyst granules falling on the conical surface can slide freely.

In some embodiments, an area of an opening at the lowermost end of the cover is greater than or equal to an area of an outlet of the riser section. Preferably, the area of the opening at the lowermost end of the cover is 1.5-5 times, more preferably 2-3 times, the area of the outlet of the reaction section.

In the disengager section of the regenerator of the present application, a cyclone is further arranged outside the cover. More than two cyclones may be arranged. Or more than two first-stage cyclones and more than two second-stage cyclones are arranged. The cyclone arranged outside the cover is communicated with a collection chamber in the disengager section of the regenerator through a raising pipe.

In some embodiments, an outlet of the raising pipe of the primary cyclone is not connected with an inlet of the first-stage cyclone.

In some embodiments, the outlet of the raising pipe of the primary cyclone is connected with the inlet of the first-stage cyclone in a bell-and-spigot manner, and there is a gap between walls of the raising pipe of the primary cyclone and the inlet of the first-stage cyclone such that the oil gas in the disengager section can enter the cyclone.

In the present application, a top end of the cover in the disengager section of the regenerator is far away from the outlet of the reaction section. In some cases, the distance between the top end of the cover and the outlet of the reaction section is approximately equivalent to the height of one cyclone. In addition, there is a cylindrical part below the truncated cone-shaped part. A part of the oil gas discharged from the outlet of the reaction section flows into the disengager section from the edge of the opening in the lower end of the cover; and the other part of the oil gas enters the cover, and directly enters the upper part of the disengager section through the inlet of the primary cyclone. In this way, compared with the oil gas which enters the disengager section and flows upward, in the present application, the oil gas flows into the cyclone from the upper and lower parts of the disengager section, so as to greatly reduce the superficial gas velocity, thereby reducing the amount of catalyst entrained by the upward flow of the oil gas and reducing the transport disengaging height (TDH).

In some embodiments, in the disengager section of the regenerator, the lowermost end of the cover is lower than the outlet of the reaction section. That is, a plane where the lowermost end of the cover is located is lower than a plane where the outlet of the reaction section is located. Thereby, the oil gas discharged from the outlet of the reaction section can enter the cover, and can also directly enter the disengager section outside the cover.

In some embodiments, the disengager section of the regenerator includes a dense phase section and a dilute phase section, and the lowermost end of the cover is higher than an interface between the dilute phase section and the dense phase section, that is, the lowermost end of the cover is located in the dilute phase section of the disengager section. Preferably, the lowermost end of the cover is higher than the interface between the dilute phase section and the dense phase section by 0.5 m or above, more preferably, 1 m or above.

In some embodiments, the inlet of the primary cyclone is not connected with the outlet of the reactor.

In some embodiments, the outlet of the raising pipe of the primary cyclone and the inlet of the first-stage cyclone are on the same horizontal plane, or the outlet of the raising pipe of the primary cyclone is higher than the inlet of the first-stage cyclone.

The reaction section of the regenerator of the present application may include a dense phase section and a riser section, both the riser section and the dense phase section are in an equal-diameter drum structure, and the diameter of the riser section is less than the diameter of the dense phase section. Also, there may be no dense phase section and riser section on the reaction section of the regenerator, the reaction section is a straight pipe, and the reaction section is a tank with an equal diameter.

In some embodiments, the primary cyclone body and the reaction section are coaxially arranged. The center line of the primary cyclone body coincides with the center line of the cover.

If only relying on inertial separation, a simple rapid separation structure is used at the outlet of the reaction section of the regenerator, and then the separation efficiency of the catalyst and the flue gas is not high. The high catalyst concentration in the flue gas entering the cyclone aggravates the consumption of the catalyst.

In addition, in the case of constant separation efficiency of the cyclone, the lower the content of the catalyst in the gas entering the cyclone is, the lower the loss of the catalyst is. Therefore, the primary separation efficiency of the flue gas and the catalyst directly affects the loss of the catalyst.

In addition to the technical features disclosed in the present application, the structures or components used in other alkane catalytic cracking reaction devices may adopt the contents and structures disclosed in the prior art to ensure the smooth proceeding of the above reaction.

Alternatively, another catalyst regeneration device of the present application includes a reaction section of the regenerator and a disengager section of the regenerator. The disengager section is communicated with the reaction section, an outlet of the reaction section is located inside the disengager section. A first splitter and a second splitter are arranged in the disengager section, and the first splitter and the second splitter are both located above the outlet of the reaction section. The first splitter is a component that reduces an upward gas velocity of a gas flow discharged from the outlet of the reaction section, the second splitter includes a second cover with openings in both upper and lower ends, a cross-sectional diameter of the opening in the lower end is greater than a cross-sectional diameter of the opening in the upper end, and the first splitter is located in the second splitter.

In the present application, at least two layers of splitters are arranged in the disengager section of the regenerator. Under the action of the first splitter closest to the outlet of the reaction section, the flue gas and the catalyst discharged from the outlet of the reaction section mostly directly settle into a dense phase bed of the disengager section. The gas is divided into two parts. A part of the gas entraining a part of the catalyst flows upward along a gap between the first splitter and the second splitter, and the other part of the gas flows obliquely upward from the outside of the second splitter. A ratio of the two parts of the gas can be flexibly adjusted by adjusting a bottom area ratio of the first splitter to the second splitter, the distance between the first splitter and the second splitter, and the size of a top outlet of the second splitter.

In some embodiments, the first splitter is a first cover, a cross-sectional area of the first cover gradually decreases from bottom to top, the cover has an opening in the lowermost end, and it is a continuous surface from the lowermost end of the cover to the top of the cover.

Preferably, the first splitter is in an inverted cone-shaped structure or a spherical cap structure.

In some embodiments, a cross-sectional area of the lowermost end of the first splitter (that is, the end closest to the outlet of the reactor) is greater than or equal to a cross-sectional area of the outlet of the reaction section. Preferably, the cross-sectional area of the lowermost end of the first splitter is greater than the cross-sectional area of the outlet of the reaction section and preferably does not exceed the cross-sectional area of the outlet of the reaction section by two times.

In an embodiment, the lowermost end of the first splitter is lower than the outlet of the reaction section. Preferably, a cross-sectional area of an annular gap formed between the outlet of the reaction section and the first splitter is less than or equal to the cross-sectional area of the outlet of the reaction section.

In another embodiment, the lowermost end of the first splitter is higher than the outlet of the reaction section. Preferably, a cross-sectional area of an annular gap formed between the outlet of the reaction section and a lower edge of the first splitter is less than or equal to the cross-sectional area of the outlet of the reaction section.

In some embodiments, the first splitter is preferably of an inverted cone-shaped structure, and an angle $\theta$ between the generatrix and the base of the cone is greater than an angle of repose of catalyst granules, thereby ensuring that the catalyst granules falling on the conical surface can slide freely.

In an embodiment, the first splitter includes a first cover in a conical structure with cross sections gradually increasing from bottom to top, edges of a cross section of the first cover passing through the cone apex in the longitudinal direction are present by two curves passing through the apex, and a curvature of each curve firstly increases and then decreases from the cone apex to a conical base edge.

In another embodiment, the first splitter includes a first cover in a conical structure with cross sections gradually increasing from bottom to top, and the conical surface of the conical structure gradually bends in a direction away from the center line of the cone from the cone apex to the cone base edge.

Further, the first splitter further includes a cavity in a conical structure with cross sections gradually increasing from top to bottom; an end, adjacent to the outlet of the reaction zone, of the cavity is the base; an end, away from the outlet of the reaction zone, of the first cover is the base, and the base edge of the first cover in the conical structure is connected to a base edge of the cavity.

Preferably, the cross-sectional area of a lowermost end of the cavity in the conical structure in the first splitter is greater than the cross-sectional area of the outlet of the reaction section. More preferably, the cross-sectional area of the lowermost end of the cavity in the conical structure in the first splitter is greater than the cross-sectional area of the outlet of the reaction section and preferably does not exceed the cross-sectional area of the outlet of the reaction section by two times.

Figure 4A:
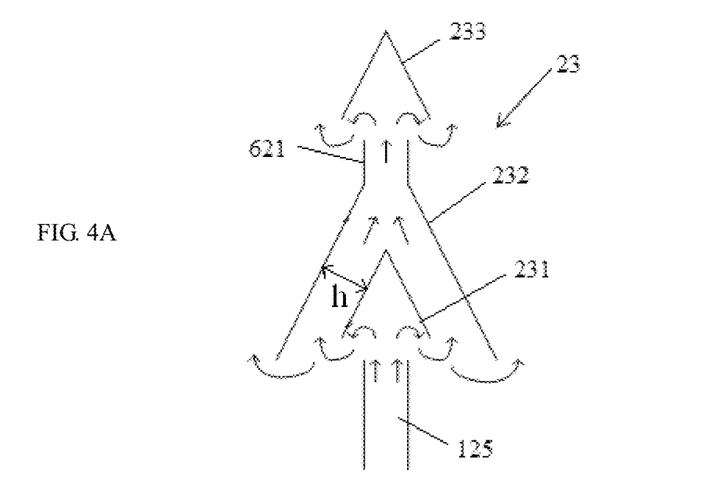
FIG. 4A-4C are cross-sectional views of a rapid separation device in a disengager section of the regenerator of the present application.
Figure 4B:
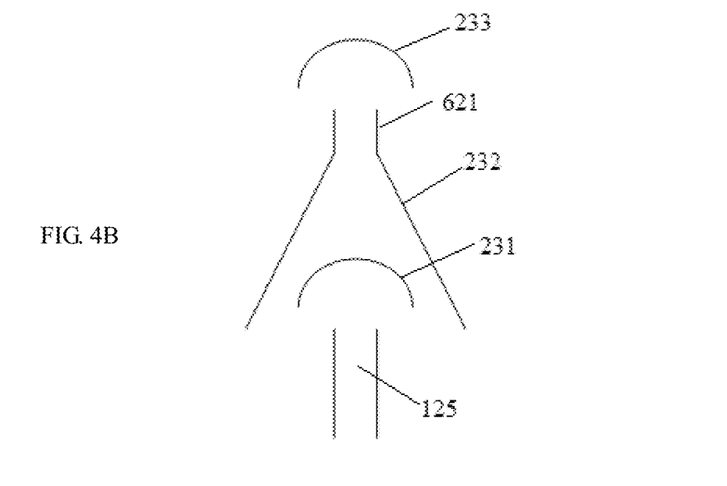
Figure 4C:
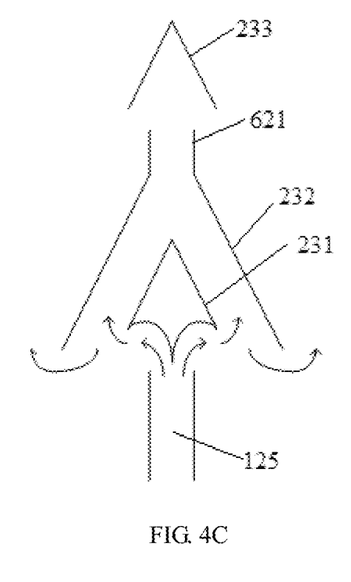

After the flue gas and the catalyst discharged from the outlet of the reaction section suffer from the first splitter as shown in FIG. 4C, most of the catalyst is prevented from entering the dense phase bed of the disengager section. The gas is divided into two parts. One part of the gas entraining part of the catalyst flows upward along the gap between the first splitter and the second splitter under the guide of the first splitter, and the other part of the gas flows obliquely upward from the outside of the second splitter.

In some embodiments, the second splitter further includes a diversion pipe with an equal diameter, and one end of the diversion pipe is connected with the opening in the upper end of the cover. Preferably, the diversion pipe is a straight pipe with an equal diameter or a conduit with a variable diameter.

In some embodiments, the second splitter is a truncated cone-shaped cover, and at least one end (the upper base) of the cross section of the truncated cone is connected to the diversion pipe.

The second splitter is a truncated cone-shaped cover, and an included angle between the generatrix and the lower base is greater than the angle of repose of the catalyst granules.

In some embodiments, the second splitter is in a spherical cap-shaped structure, and the spherical cap-shaped structure is provided with an outlet. Preferably, an uppermost end (that is, away from the outlet of the reactor) of the spherical cap-shaped structure is provided with an outlet.

The area of the outlet of the second splitter is designed such that a gas velocity at the outlet is less than or equal to a gas velocity at the outlet of the riser section. That is, the cross-sectional area of the outlet of the second splitter is greater than the cross-sectional area of the outlet of the reaction section.

In some embodiments, a cross-sectional area of a lowermost end of the second splitter is greater than 1.5 times the maximum cross-sectional area of the first splitter.

In some embodiments, the minimum distance between the first splitter and the second splitter is greater than a cross-sectional diameter of the outlet of the reaction section.

By controlling or changing the distance between the first splitter and the second splitter, a ratio (split ratio) of fluid directly entering the disengager section to fluid continuing flowing upward through the gap between the first splitter and the second splitter can be adjusted. Preferably, the ratio of the two splits is preferably 3/1-1/1.

In addition, the lowermost end of the second splitter is higher than the interface between the dilute phase and the dense phase of the catalyst in the disengager section. More preferably, the lowermost end of the second splitter is higher than the interface between the dilute phase and the dense phase of the catalyst in the disengager section by at least 1 m.

In some embodiments, a third splitter is further arranged in the disengager section, the third splitter is located above the second splitter, the third splitter is also a third cover whose cross-sectional area gradually decreases from bottom to top, the cover has an opening in the lowermost end, and it is a continuous surface from the lowermost end of the cover to the top of the cover.

Preferably, the third splitter is in an inverted cone-shaped structure or a spherical cap structure.

Figure 5:
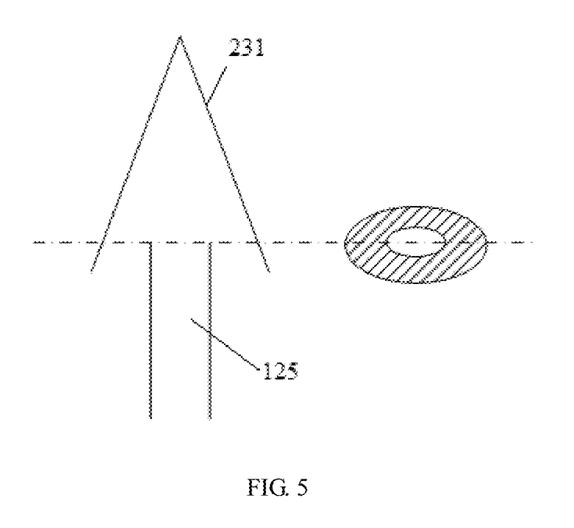
FIG. 5 is a cross-sectional view of another rapid separation device of the disengager section of the regenerator of the present application.

The catalyst-entrained gas flows upward in the diversion pipe of the second splitter. Under the action of the third splitter, a part of the catalyst directly settles and falls, and the other part of the catalyst continues to be entrained by the gas. However, the gas flowing out from here generally flows horizontally or obliquely downward towards the inlet of the cyclone (as shown in FIG. 5), and there is no upward force to balance the gravity of the catalyst, so that this part of the catalyst also naturally settles. It can be seen that the combined arrangement of multiple layers of splitters further reduces the entrainment of the catalyst and promote the settling of the catalyst by changing the flow field distribution.

In some embodiments, the cross-sectional area of the lowermost end of the third splitter is greater than or equal to the cross-sectional area of the outlet of the second splitter. Or the cross-sectional area of the lowermost end of the third splitter is greater than or equal to the cross-sectional area of the outlet of the diversion pipe in the second splitter.

In some embodiments, the lowermost end of the third splitter is lower than the outlet of the diversion pipe of the second splitter. Preferably, a cross-sectional area of an annular gap formed between the outlet of the diversion pipe and the third splitter is greater than or equal to the cross-sectional area of the outlet of the diversion pipe. Preferably, the cross-sectional area of the annular gap formed between the outlet of the diversion pipe and the third splitter is greater than the cross-sectional area of the outlet of the reactor.

In another embodiment, the lowermost end of the third splitter is positionally higher than the outlet of the diversion pipe of the second splitter. Preferably, a cross-sectional area of an annular gap formed between the outlet of the diversion pipe and a lower edge of the third splitter is greater than or equal to the cross-sectional area of the outlet of the diversion pipe. Preferably, the cross-sectional area of the annular gap formed between the outlet of the diversion pipe and the third splitter is greater than the cross-sectional area of the outlet of the reaction section.

In some embodiments, the third splitter is preferably in an inverted cone-shaped structure, and an included angle θ between the generatrix and the base of the cone is greater than the angle of repose of the catalyst granules, thereby ensuring that the catalyst granules falling on the conical surface can slide freely.

In the present application, the first, second and third splitters are respectively mounted in the disengager section of the regenerator in a connection manner commonly used in the field.

In the disengager section of the regenerator of the present application, a cyclone is further arranged outside the first splitter, the second splitter and the third splitter. More than two cyclones may be arranged. Or more than two first-stage cyclones and more than two second-stage cyclones may be arranged. The cyclone arranged outside the cover communicates with the collection chamber in the disengager through the raising pipe.

In some embodiments, the outlet of the second splitter or the outlet of the diversion pipe is higher than or equal to the inlet of the cyclone in height.

In some embodiments, inlets of more than two cyclones in the disengager section of the regenerator are arranged close to the wall of the disengager section of the regenerator. Preferably, the inlets of the cyclones are arranged in a circumferential direction, for example, the inlets of the cyclones are arranged in a clockwise direction or a counterclockwise direction.

Through this cyclone arrangement manner of the present application, the gas in the whole disengager section of the regenerator rotates in the same direction, which is beneficial for the catalyst suspended in the disengager section to be "flung" to the wall of the disengager section under the action of centrifugal force and to slide down the wall to enter the dense phase bed, thereby further reducing the amount of the catalyst entering the cyclone.

In the present application, the flue gas flows into the cyclone from the upper and lower parts of the disengager section, so that the superficial gas velocity is greatly reduced, thereby reducing the amount of catalyst entrained by the upward flowing of the flue gas and reducing the transport disengaging height (TDH).

The following is a further description in conjunction with specific drawings and specific examples.

Example 1

200 kg cracking catalyst was prepared by a spray granulation method.

143 kg of deionized water and 96 kg of pseudo-boehmite (reduced by 35 wt % according to the circumstance) were added into a stirred tank, 8 kg of 68% concentrated nitric acid was added under constant stirring for mixing to obtain a mixture in a gel state. Then 310 kg of silica sol (with a solid content of 40 wt %), 1.5 kg of sodium carbonate, 3.5 kg of calcium carbonate, 0.5 kg of nickel nitrate and 1.1 kg of ferric nitrate were added. After stirring for 1 h, spray granulation was performed to obtain a catalyst, and the obtained catalyst was calcined at 700° C. to obtain a finished product for later use.

The above catalyst has good thermal and hydrothermal stability, suitable acidity, small surface area (the specific surface area is not greater than 150 $m^2/g$, and is not greater than 80 $m^2/g$ in some cases), and high mechanical strength.

Example 2

In this example, a method for preparing low-carbon olefins from naphtha includes the following steps:

S1: a catalyst enters a pre-lift pipe through a regenerator sloped pipe and flows upward under the action of a pre-lift medium to enter a dense phase section of the reactor, and naphtha and steam are sprayed into a reactor tangentially upward through nozzles located at a bottom of the dense phase section of the reactor;

the reactor nozzles spray the naphtha and the steam along a tangential direction of a cross-sectional circular ring and at an angle of 10-90° to a vertical direction;

S2: oil gas and the catalyst leaving a riser pipe enter a disengager of a reaction device, the oil gas leaves the disengager to enter a separation system, and the catalyst flows out through a conveying part of the cyclone and falls into a stripping section of the disengager;

S3: the catalyst is stripped and enters a regenerator through a spent sloped pipe, and the catalyst is heated in the regenerator; and S4: the catalyst enters a disengager section of the regenerator, falls into the stripping section of the disengager section of the regenerator and enters a degassing tank, the catalyst is further stripped in the degassing tank, and then the stripped catalyst returns to the reactor through the regenerator sloped pipe.

In S1, the nozzles spray the naphtha and the steam at an angle of 30-60° to the vertical direction, and a linear velocity at an outlet is greater than 10 m/s.

The nozzles are arranged equidistantly in the same section, and the number of the nozzles is 2-6.

The catalyst includes aluminosilicate, alkali metal oxide, alkaline earth metal oxide, $TiO_2$, iron oxide, vanadium oxide and nickel oxide.

Mass percentages of components in the catalyst are as follows:

the aluminosilicate includes $SiO_2$ and $Al_2O_3$, wherein the mass percentage of $SiO_2$ is 30-80 wt %, and the mass percentage of $Al_2O_3$ is 10-70 wt %;

the alkali metal oxide includes one or two of $Na_2O$ and $K_2O$, wherein a mass percentage of the alkali metal oxide is not greater than 5 wt %; and the alkaline earth metal oxide includes one or two of CaO and MgO, wherein a mass percentage of the alkaline earth metal oxide is not greater than 5 wt %.

The mass percentages of $TiO_2$, the iron oxide, the vanadium oxide and the nickel oxide are not greater than 2 wt %.

In S1, the pre-lift medium is steam and ethane. A mass ratio of the steam to the ethane is in a range from 1/20 to 1/1.

In S1, a mass ratio of the steam to the naphtha is in a range from 1/20 to 1/1.

In S1, an average gas velocity in the dense phase section is greater than 0.25 m/s.

In S1, an average retention time of the oil gas in the dense phase section is not more than 4 s.

In S2, an average gas velocity in the riser pipe is greater than 3 m/s.

Example 3

Figure 1:
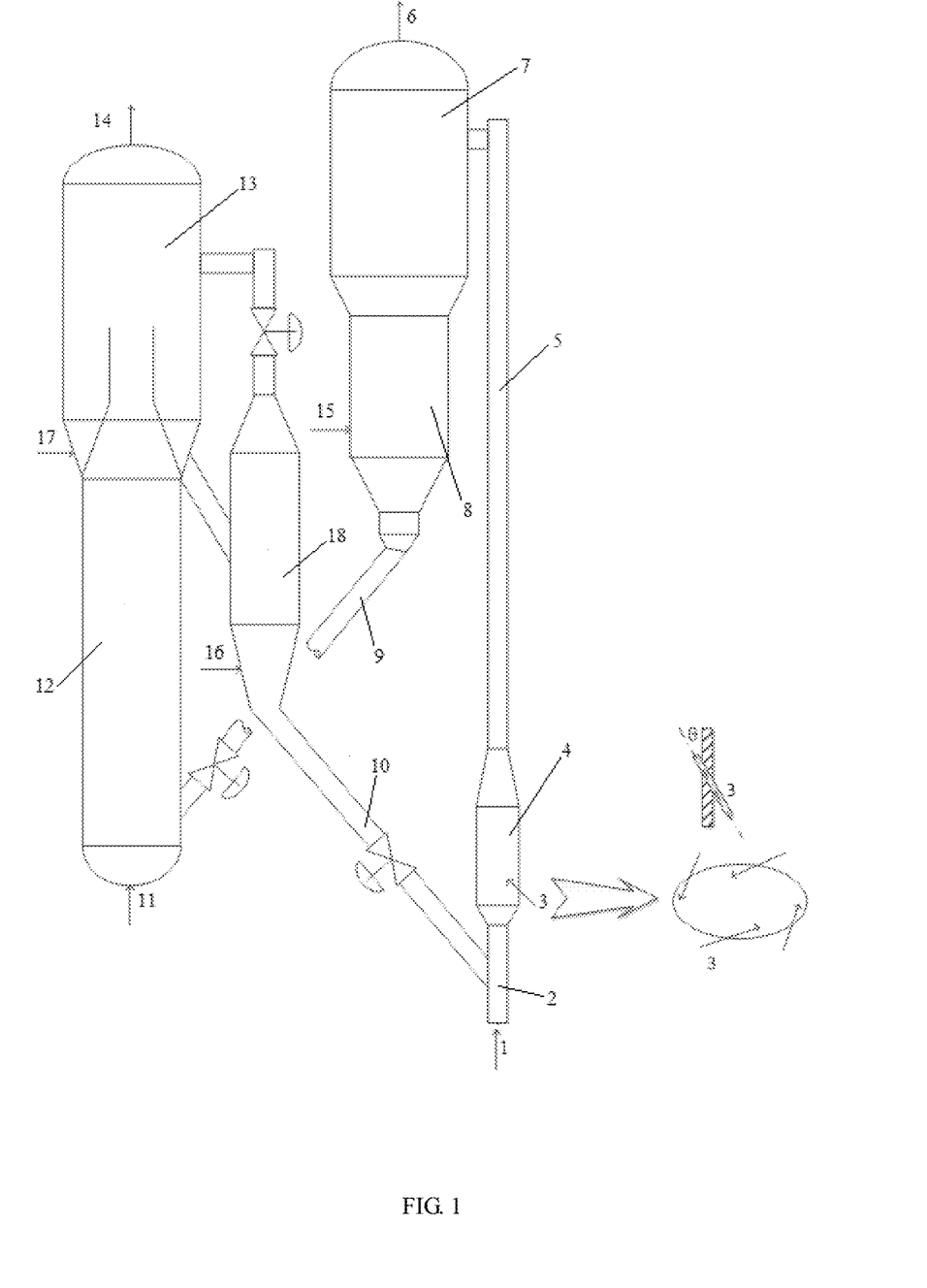
FIG. 1 is a schematic diagram of a naphtha catalytic cracking reaction-regeneration device of the present application.

A device for implementing the method described in Example 2 at least includes:

a pre-lift pipe 2, a dense phase section of a reactor 4, a first end of which communicated with the pre-lift pipe 2, a regenerator sloped pipe 10, communicated with an inner of the pre-lift pipe 2, a nozzle 3, located at a bottom of the dense phase section of the reactor 4, a riser pipe 5, communicated with a second end of the dense phase section of the reactor 4, a disengager disengager section 7, communicated with the riser pipe 5, a disengager stripping section 8, communicated with the disengager disengager section 7, a spent sloped pipe 9, communicated with the disengager stripping section 8, and a degassing tank 18, connected with the spent sloped pipe 9 and the regenerator 12.

Specific steps of using the device to produce low-carbon olefins are as follows:

As shown in FIG. 1, the high-temperature regenerated catalyst enters the pre-lift pipe 2 through the regenerator sloped pipe 10 and flows upward under the action of a pre-lift medium 1 to enter the dense phase section of the reactor 4, and the feedstock, naphtha, and steam are sprayed into the reactor through the nozzle 3 located at the bottom of the dense phase section of the reactor 4. With reference to an enlarged view of the nozzle arrangement in FIG. 1, the nozzle sprays the feedstock along a tangential direction of a cross-sectional circular ring of the reactor and at an angle of 30-60° to a vertical direction. The linear velocity at the outlet of the nozzle is greater than 5 m/s, so that the catalyst can be driven to rotate to enhance the mass transfer, heat transfer and reaction between the oil gas and the catalyst and thus reduce the stagnant section in the dense phase section, thereby reducing or avoiding coking in the reactor. An average gas velocity in the dense phase section is greater than 0.25 m/s. An average retention time of the oil gas in the dense phase section is not more than 4 s. The oil gas leaves the dense phase section and enters the riser pipe 5, an average gas velocity in the riser pipe 5 is greater than 3 m/s, and an average retention time in the riser pipe 5 is not more than 5 s. The oil gas 6 and the catalyst leaving the riser pipe 5 directly enter cyclones in the disengager section 7 and are subjected to two to three stages of separation, the oil gas leaves the disengager to enter a separation system, and the catalyst flows out through a conveying part of the cyclone and falls into the disengager stripping section 8. A large amount of oil gas is not allowed to enter the disengager in order to prevent the high-temperature oil gas from coking in the disengager. The catalyst is stripped by steam 15, and then the stripped catalyst enters the regenerator 12 through the spent sloped pipe 9. In the regenerator 12, the sprayed air and fuel 11 are burned to heat a regenerant to reach a high temperature of 750-850° C., and at the same time, the coke on the catalyst surface is burnt off. The high-temperature catalyst is driven by the flue gas to enter a regeneration disengager 13, falls into the regenerator stripping section, and is stripped by steam 17, and then the stripped catalyst enters the degassing tank 18. The catalyst is further stripped by steam 16 in the degassing tank 18, and the stripped catalyst returns to the reactor through the regenerator sloped pipe 10.

Example 4

The components of naphtha (marked as No. 1) in this example are as shown in Table 1, and a naphtha cracking reaction is performed on a fluidized bed device in Example 3.

In the method, the catalyst regeneration temperature is 800° C., and the pre-lift medium is steam, which accounts for 5 wt % of the naphtha by mass. The catalyst includes the following oxides: 51 wt % of $SiO_2$, 42 wt % of $Al_2O_3$, 4 wt % of MgO, 0.5 wt % of $Fe_2O_3$, 1.5 wt % of $Na_2O$ and 1.0 wt % of $V_2O_5$. The temperature of the outlet of the riser pipe is controlled to be 700° C., and a mass ratio of the steam to the naphtha is 1/4. An average retention time of the oil gas in the dense phase section of the reactor is 1.5 s, and an average retention time of the oil gas in the riser pipe is 1.5 s. The results show that the yield of ethylene and propylene is 47 wt %, and the specific cracking product distribution is as shown in Table 3.

When a steam cracking method in the prior art is used to crack the same naphtha, the yield of ethylene and propylene is about 43 wt %.

TABLE 1

Composition of Naphtha No. 1 of Example 4, wt %

| Carbon number | N-alkanes | Isoalkanes | Cycloalkanes | Arenes | Olefins | Total |
|---|---|---|---|---|---|---|
| 5 | 8.09 | 6.74 | 1.42 | — | 0.02 | 16.27 |
| 6 | 12.10 | 12.02 | 8.53 | 1.58 | 0.01 | 34.24 |
| 7 | 7.09 | 9.27 | 9.65 | 5.62 | — | 31.62 |
| 8 | 2.12 | 2.78 | 2.84 | 3.17 | — | 10.92 |
| 9 | 0.72 | 1.06 | 0.97 | 0.61 | — | 3.37 |
| 10 | 0.51 | 0.50 | 0.66 | 0.46 | — | 2.14 |
| 11 | — | 0.28 | — | 1.18 | — | 1.45 |
| Σ | 30.64 | 32.64 | 24.07 | 12.62 | 0.03 | 100 |

Example 5

Example 5 differs from Example 4 in that: the temperature of the outlet of the riser pipe is increased to 750° C., and other conditions are the same as those in Example 4. The yield of ethylene and propylene is 52.32 wt %, and the specific cracking product distribution is as shown in Table 3.

Example 6

This example differs from Example 4 in that: the components of naphtha are different, the components of naphtha (marked as No. 2) in this example are as shown in Table 2, and other conditions are the same as those in Example 4. The yield of ethylene and propylene is 50.48 wt %, and the specific cracking product distribution is as shown in Table 3.

TABLE 2

Composition of Naphtha No. 2 of Example 6, wt %

| Carbon number | N-alkanes | Isoalkanes | Cycloalkanes | Arenes | Olefins | Total |
|---|---|---|---|---|---|---|
| 5 | 10.96 | 5.62 | 1.20 | — | — | 17.78 |
| 6 | 10.37 | 12.32 | 5.47 | 0.93 | — | 29.09 |
| 7 | 6.34 | 6.83 | 5.16 | 1.70 | — | 20.03 |
| 8 | 3.52 | 4.07 | 3.65 | 1.67 | 0.08 | 12.92 |
| 9 | 2.05 | 4.01 | 1.89 | 1.08 | — | 9.13 |
| 10 | 1.39 | 1.90 | 2.63 | 2.54 | — | 8.45 |
| 11 | 0.08 | 1.51 | — | 0.28 | — | 1.87 |
| 12 | 0.11 | — | — | 0.61 | — | 0.73 |
| Σ | 34.82 | 36.27 | 20.00 | 8.82 | 0.08 | 100 |

Example 7

This example differs from Example 4 in that: the components of naphtha are different, the components of naphtha (marked as No. 2) in this example are as shown in Table 2, and the temperature of the outlet of the riser pipe is increased to 750° C. Other conditions are the same as those in Example 4. The yield of ethylene and propylene is 55.20 wt %, and the specific cracking product distribution is as shown in Table 3.

Example 8

This example differs from Example 4 in that: the components of naphtha (marked as No. 2) in this example are as shown in Table 2, and the temperature of the outlet of the riser pipe is increased to 750° C.; ethane accounting for 3 wt % of the naphtha is mixed in the feedstock; and ethane and steam are together used as the pre-lift medium, wherein the steam accounts for 1.5 wt % of the naphtha feedstock. Other conditions are the same as those in Example 4. The yield of ethylene and propylene is 57.65 wt %, and the specific cracking product distribution is as shown in Table 3.

TABLE 3

Naphtha Catalytic Cracking Product Distribution, wt %

| | Example | | | | |
|---|---|---|---|---|---|
| Feedstock | 4<br>Naphtha<br>No. 1 | 5<br>Naphtha<br>No. 1 | 6<br>Naphtha<br>No. 2 | 7<br>Naphtha<br>No. 2 | 8<br>3%<br>ethane/<br>97%<br>naphtha<br>No. 2 |
| Outlet temperature, ° C. | 700 | 750 | 700 | 750 | 750 |
| Hydrogen | 0.70 | 1.05 | 0.91 | 0.91 | 0.91 |
| Methane | 10.26 | 16.05 | 12.45 | 16.74 | 16.94 |
| Ethane | 2.47 | 2.49 | 2.81 | 3.01 | 0.30 |
| Ethylene | 26.49 | 34.69 | 31.22 | 37.96 | 40.31 |
| Propane | 0.59 | 0.60 | 0.52 | 0.44 | 0.45 |
| Propylene | 21.14 | 17.63 | 19.25 | 17.24 | 17.34 |
| Isobutane | 0.50 | 0.47 | 0.78 | 0.34 | 0.35 |
| n-butane | 1.99 | 0.18 | 0.29 | 0.19 | 0.19 |
| Trans-butene | 5.16 | 2.93 | 4.94 | 4.25 | 4.58 |
| 1-butene | 1.83 | 0.72 | 1.23 | 0.65 | 0.66 |
| Isobutene | 4.18 | 2.55 | 2.82 | 2.09 | 2.10 |
| Cis-2-butene | 1.75 | 0.69 | 1.06 | 0.61 | 0.62 |
| 1,3-butadiene | 4.24 | 4.65 | 5.00 | 5.05 | 5.08 |
| Gasoline | 13.86 | 11.73 | 11.78 | 7.22 | 7.06 |
| Diesel | 4.83 | 3.58 | 4.95 | 3.28 | 3.10 |
| Ethylene + propylene | 47.63 | 52.32 | 50.48 | 55.20 | 57.65 |

Example 9

This example describes a partial structure of a catalyst regeneration device of the naphtha catalytic cracking reaction device. A further specific description is provided below in conjunction with FIG. 2 and FIG. 3.

Figure 2:
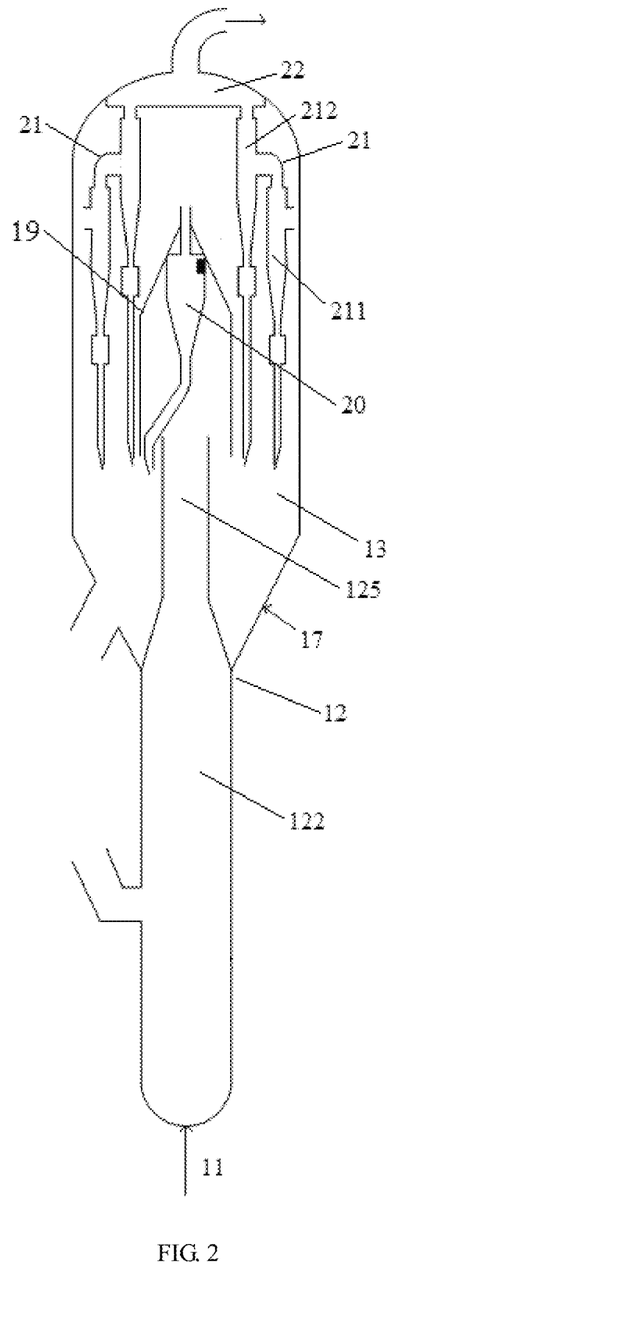
FIG. 2 is a schematic diagram of a naphtha catalytic cracking reaction device of the present application.

As shown in FIG. 2, the naphtha catalytic cracking catalyst regeneration device includes a regeneration reactor 12 and a regeneration disengager 13. The regeneration reactor 12 includes a dense phase section 122 and a riser section 125, and the riser section 125 extends into the regeneration disengager 13.

Figure 3:
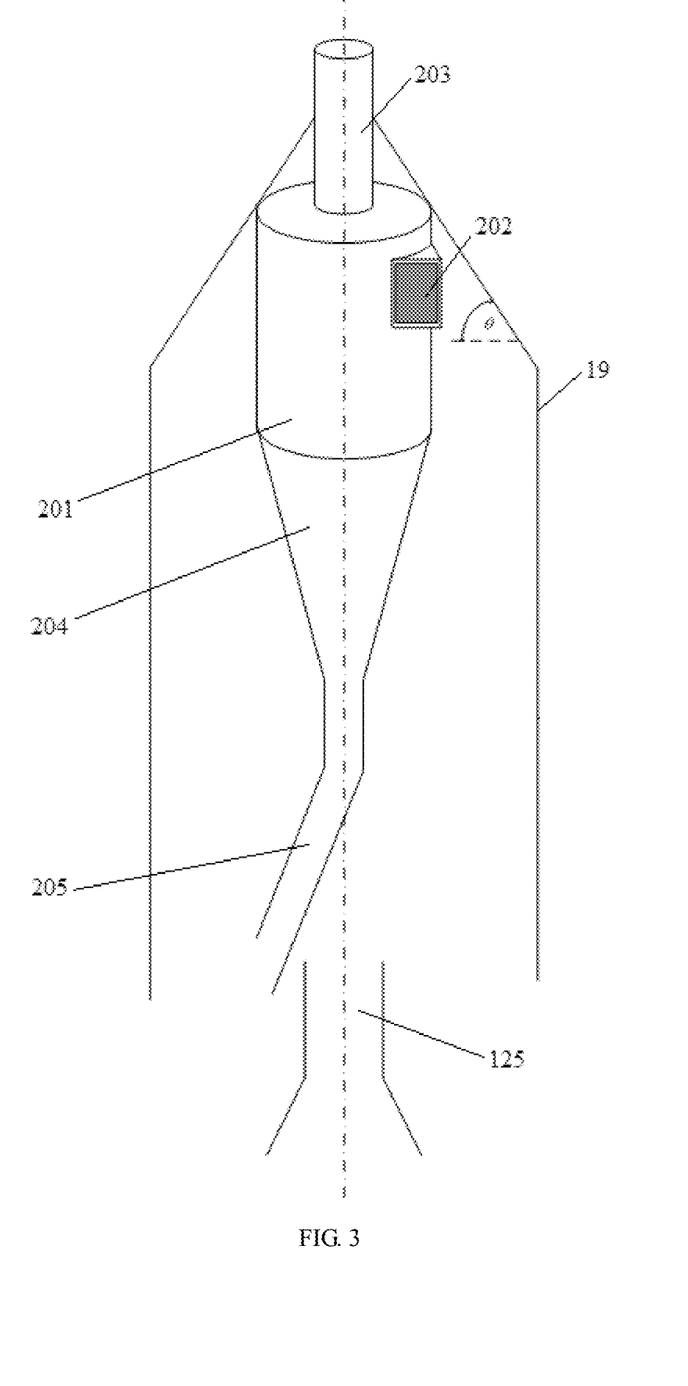
FIG. 3 is a schematic structural diagram of a cover and a primary cyclone in a disengager section of the regenerator in FIG. 2.

A cyclone rapid separation component is arranged in the regeneration disengager 13. The cyclone rapid separation component includes a primary cyclone 20 and a cover 19. As shown in FIG. 3, the primary cyclone 20 sequentially includes a cylinder 201, an inverted cone 204 and a conveying part 205 from top to bottom. An inlet 202 of the primary cyclone 20 is arranged on an upper part of the cylinder 201, and a gas flow enters the primary cyclone 20 along a tangential direction from the inlet 202. A top of the primary cyclone 20 is provided with a raising pipe 203 which communicated with the primary cyclone 20, so that the oil gas or flue gas entering the primary cyclone 20 is discharged through the raising pipe 203. The cover 19 includes two parts, an upper part is in the shape of a truncated cone, a lower part is in the shape of a cylinder, and the cover may be integrally formed. An edge of an upper end (that is, an upper base of the truncated cone) of the cover 19 is connected with a periphery of the raising pipe 203, and the primary cyclone 20 is arranged in the cover. A lower end surface of the cover 19 is lower than an outlet of the riser section 125, and is located in a dilute phase section of the disengager.

An included angle between the generatrix of the truncated cone-shaped upper part and a lower base of the truncated cone-shaped upper part of the cover 19 is greater than an angle of repose of catalyst granules. In other words, the size of the included angle of the truncated cone is related to the angle of repose of the catalyst granules used, and can ensure that the catalyst flows downward.

A cross-sectional area of an opening in the lower end of the cover 19 is greater than a cross-sectional area of an outlet of the riser section 125.

In this example, center lines of the cylinder 201 and the inverted cone 204 of the primary cyclone 20, the cover 19 and the regeneration reactor 12 coincide. An outlet of the conveying part should be far away from the outlet of the riser section 125, that is, if the outlet of the conveying part is close to the outlet of the riser section 125, it is not conducive for the catalyst of the primary cyclone 20 to be discharged from the conveying part due to the upward gas flow of the riser section 125.

In this example, the inlet 202 of the primary cyclone 20 is not connected with the outlet of the riser section 125.

In the disengager 13, a space outside the cover 19 is further provided with cyclones 21 and a collection chamber 22. In this example, two sets of cyclones are arranged. Each set of cyclones includes a first-stage cyclone 211 and a second-stage cyclone 212, and the second-stage cyclone 212 is communicated with the collection chamber 22 through the raising pipe. An inlet of the first-stage cyclone 211 and the inlet 202 of the primary cyclone 20 are on the same horizontal plane, or the inlet of the first-stage cyclone 211 is slightly lower than the inlet 202 of the primary cyclone 20.

Example 10

This example is another embodiment of the partial structure of the naphtha catalytic cracking catalyst regeneration device. A further specific description is provided below in conjunction with FIGS. 4-7.

As shown in FIG. 2, the naphtha catalytic cracking catalyst regeneration device includes a regeneration reactor 12 and a regeneration disengager 13. The regeneration reactor 12 includes a dense phase section and a riser section 125, and the riser section 125 extends into the regeneration disengager 13.

A cyclone rapid separation component 23 is arranged in the disengager 13. The cyclone rapid separation component 23 includes a first splitter 231 and a second splitter 232, and further includes a third splitter 233. The first, second and third splitters are located above an outlet of the regeneration reactor.

The cyclone rapid separation component can achieve the effect of rapid separation of the flue gas and the catalyst in the present application when only including the first splitter 231 and the second splitter 232. In the case that cyclone rapid separation component includes the third splitter 233, the better separation effect may be achieved.

The first splitter 231 may be a conical first cover as shown in FIG. 4A, or a spherical cap-shaped first cover as shown in FIG. 4B, or, may be a first cover in a structure as shown in FIG. 4C. The first splitter 231 as shown in FIG. 4C is composed of two parts, an upper part is in a conical structure, and a lower part is the first cover whose diameter gradually increases from bottom to top. A longitudinal section of the first cover passing through its center line is present by two curves that pass through the apex and bend in a direction away from the center line, and a curvature of the curve firstly increases and then decreases from bottom to top. A base edge at a lowermost end of the conical structure of the upper part is connected with a periphery of an uppermost end of the lower part. The upper and lower parts may also be integrally formed.

As shown in FIGS. 4A, 4B and 4C, the second splitter 232 includes a truncated cone-shaped structure and a diversion pipe 621, the diversion pipe 621 is connected with the minimum cross section of the truncated cone-shaped structure, or the diversion pipe 621 and the truncated cone-shaped structure are integrally formed to form the second splitter 232. The first splitter 231 is located inside the second splitter 232.

The structure of the third splitter 233 is similar to the structure of the first splitter 231. The shapes of the first and third splitters may be the same or different. For example, the first splitter 231 is in a spherical cap-shaped structure, and the third splitter 233 may be in a conical structure.

An included angle between the generatrix and the lower base of the cone of the first or third splitters (231, 233) is greater than an angle of repose of catalyst granules. In other words, the size of the included angle of the cone is related to the angle of repose of the catalyst granules used, and can ensure that the catalyst flows downward.

If the first splitter 231 is the first cover in a conical or spherical cap-shaped structure, a cross-sectional area of the lowermost end (that is, the end closest to the outlet of the reactor) of the first splitter is greater than or equal to a cross-sectional area of the outlet of the riser section 125 of the regeneration reactor. Preferably, the cross-sectional area of the lowermost end of the first splitter is greater than the cross-sectional area of the outlet of the riser section 125 of the regeneration reactor and preferably does not exceed the cross-sectional area of the reactor riser section 125 by two times.

When the first splitter 231 is the structure as shown in FIG. 4C, a cross-sectional area of the lowermost end of the conical structure of its upper part is greater than the cross-sectional area of the outlet of the riser section 125 of the regeneration reactor and preferably does not exceed the cross-sectional area of the riser section 125 of the regeneration reactor by two times.

In this example, the lowermost end of the first splitter 231 is higher than the outlet of the riser section 125 of the regeneration reactor. A cross-sectional area of an annular gap formed between the outlet of the riser section 125 of the regeneration reactor and a lower edge of the first splitter 231 is less than or equal to the cross-sectional area of the outlet of the riser section 125 of the regeneration reactor.

The lowermost end of the first splitter 231 may also be lower than the outlet of the riser section 125 of the regeneration reactor. As shown in FIG. 5, the cross-sectional area of the annular gap formed between the outlet of the riser section 125 of the regeneration reactor and the first splitter (dashed area in FIG. 5) is less than or equal to the cross-sectional area of the outlet of the riser section 125 of the regeneration reactor.

In this example, the maximum cross-sectional area of the truncated cone-shaped structure of the second splitter 232 is greater than the cross-sectional area of the lowermost end of the first splitter 231 by 1.5 times. The minimum distance of a gap between the first splitter 231 and the second splitter 232 should be greater than a cross-sectional diameter of the outlet of the riser section 125 of the regeneration reactor.

In this example, the cross-sectional area of the lowermost end of the third splitter 233 is greater than or equal to the cross-sectional area of the outlet of the diversion pipe 621 in the second splitter 232. The lowermost end of the third splitter is higher than the outlet of the diversion pipe of the second splitter. Preferably, a cross-sectional area of an annular gap formed between the outlet of the diversion pipe and a lower edge of the third splitter is greater than or equal to the cross-sectional area of the outlet of the diversion pipe.

Figure 7:
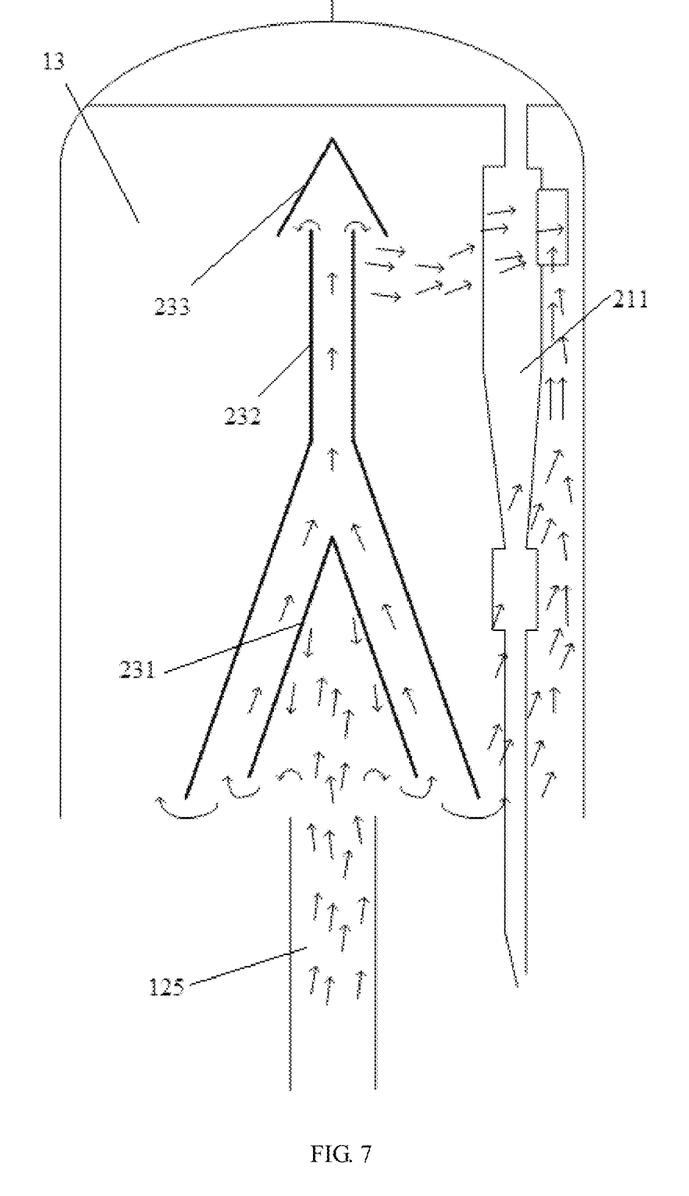
FIG. 7 is a schematic diagram of flowing of flue gas in a disengager section of the regenerator of the present application.

In this example, cyclones 21, including at least two first-stage cyclones 211 and at least two second-stage cyclones 212, are arranged in the disengager 13 and outside the cyclone rapid separation component 23, and the second-stage cyclones 212 is communicated with a collection chamber 22 through a raising pipe. An inlet of the first-stage cyclone 211 and an inlet of the diversion pipe 621 of the second splitter 232 are on the same horizontal plane, or the inlet of the first-stage cyclone 211 is slightly lower than the inlet of the diversion pipe 621. As shown in FIG. 7, the catalyst-entrained gas flows upward in the diversion pipe 621 of the second splitter 232. Under the action of the third splitter 233, a part of the catalyst directly settles and falls, and the other part of the catalyst flows out from the lower part of the third splitter along with the gas. The gas generally flows horizontally or obliquely downward towards the inlet of the cyclone, and the catalyst naturally settles in the absence of upward acting force.

Figure 6:
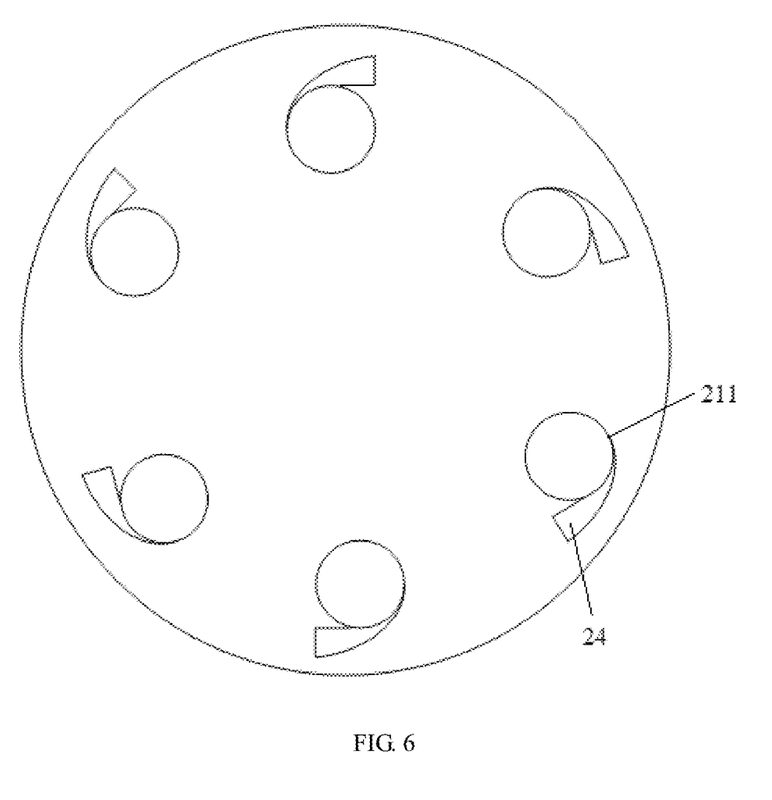
FIG. 6 is a top view inside a disengager section of the regenerator of the present application.

As shown in FIG. 6, a plurality of cyclones are uniformly arranged along a circumferential direction of the disengager 13, the inlet of the first-stage cyclone 211 is arranged close to the wall of the disengager 13, and the inlets 24 of all the cyclones 211 are arranged in the counterclockwise direction on the circumference.

A detailed description has been made to the present application. It is intended to make those skilled in the art to understand and implement the content of the present application, rather than limiting the protection scope of the present application. All equivalent changes or modifications made according to the spirit and essence of the present application shall be covered by the protection scope of the present application.

The invention claimed is:

1. A method for catalytic cracking of naphtha, comprising:
S1: delivering a catalyst in a pre-lift pipe through a regenerator sloped pipe and to flow upward under the action of a pre-lift medium to enter a dense phase section of a reactor,
feeding a feedstock containing naphtha into the reactor tangentially upward through a nozzle located at a bottom of the dense phase section of the reactor;
feeding the feedstock, by the nozzle of the reactor, along a tangential direction of a circular cross-sectional of the dense phase section of the reactor at an angle of 10-90° to a vertical direction;
S2: enabling oil gas and the catalyst from a riser pipe to enter a settler of a reaction device,
enabling the oil gas from the disengager to enter a separation system, and enabling the catalyst to flow out through a conveying part of a cyclone to fall into a settler stripping section;
S3: stripping the catalyst, enabling the catalyst stripped to enter a regenerator through a spent sloped pipe, and heating the catalyst in the regenerator; and
S4: enabling the catalyst to enter a disengager section of the regenerator to fall into a stripping section of the disengager section of the regenerator and enter a degassing tank, and
stripping the catalyst in the degassing tank and enabling the catalyst stripped to return to the reactor through the regenerator sloped pipe,
wherein the regenerator comprises:
a reaction section of the regenerator and a disengager section of the regenerator, wherein
the reaction section of the regenerator comprises a dense phase section and a riser section, an outlet of the dense phase section is connected with an inlet of the riser section, an outlet of the riser section of the reaction section of the regenerator is located in the disengager section of the regenerator, and
a primary cyclone, a raising pipe of the primary cyclone and a cover are arranged in the disengager section of the regenerator;
the primary cyclone comprises a primary cyclone body and a conveying part, the conveying part is located below the primary cyclone body, and the raising pipe is located above and communicated with the primary cyclone body;
the primary cyclone is arranged in the cover, and there is no overlap between the outlet of the conveying part and the outlet of the riser section in an axial direction of the disengager section;
the cover comprises an upper part and a lower part, the upper part of the cover is a truncated cone, the lower part of the cover is below a lower base of the truncated cone, and the lower part of the cover is a cylindrical structure;
an outlet of the riser section of the reaction section of the regenerator is located in the cover;
an area of an opening in a lowermost end of the cover is greater than an area of an outlet of the reaction section; and
a circumference of an upper base of the truncated cone is connected with a periphery of the raising pipe of the primary cyclone, or the circumference of the upper base of the truncated cone is connected with a periphery of the primary cyclone above an inlet of the primary cyclone.

2. The method according to claim 1, wherein the catalyst comprises aluminosilicate, alkali metal oxide, alkaline earth metal oxide, $TiO_2$, iron oxide, vanadium oxide and nickel oxide.

3. The method according to claim 1, wherein in the step S1, the pre-lift medium is steam and ethane, a mass ratio of the steam to the ethane is in a range from 1/20 to 1/1, more preferably in a range from 1/10 to 1/2.

4. The method according to claim 1, wherein in the step S1, the feedstock comprises naphtha and steam, and a mass ratio of the steam to the naphtha is in a range from 1/20 to 1/1.

5. The method according to claim 2, wherein in mass percentages of components in the catalyst, a mass percentage of the alkali metal oxide is not greater than 5 wt %, a mass percentage of the alkaline earth metal oxide is not greater than 5 wt %.

6. The method according to claim 2, wherein mass percentage of the $TiO_2$, the iron oxide, the vanadium oxide or the nickel oxide is not greater than 2 wt % respectively.

7. The method according to claim 1, wherein an edge of the upper base of the circular truncated cone of the cover is connected with the periphery of the primary cyclone above the inlet of the primary cyclone.

8. The method according to claim 1, wherein an angle θ between the generatrix of the truncated cone and the lower base of the truncated cone of the cover is greater than an angle of repose of catalyst granules.

9. The method according to claim 1, wherein the area of the opening in the lowermost end of the cover is greater than or equal to an area of the outlet of the riser section.

10. The method according to claim 1, wherein in the disengager section of the regenerator, the lowermost end of the cover is lower than an outlet of a riser pipe of the reaction section.

11. The method according to claim 1, wherein an outlet of the conveying part of the primary cyclone is lower than the outlet of the riser pipe of the reaction section.

12. A method for catalytic cracking of naphtha, comprising:
S1: delivering a catalyst in a pre-lift pipe through a regenerator sloped pipe and to flow upward under the action of a pre-lift medium to enter a dense phase section of a reactor,
feeding a feedstock containing naphtha into the reactor tangentially upward through a nozzle located at a bottom of the dense phase section of the reactor;
feeding the feedstock, by the nozzle of the reactor, along a tangential direction of a circular cross-sectional of the dense phase section of the reactor at an angle of 10-90° to a vertical direction;
S2: enabling oil gas and the catalyst from a riser pipe to enter a settler of a reaction device,
enabling the oil gas from the disengager to enter a separation system, and enabling the catalyst to flow out through a conveying part of a cyclone to fall into a settler stripping section;
S3: stripping the catalyst, enabling the catalyst stripped to enter a regenerator through a spent sloped pipe, and heating the catalyst in the regenerator; and
S4: enabling the catalyst to enter a disengager section of the regenerator to fall into a stripping section of the disengager section of the regenerator and enter a degassing tank, and stripping the catalyst in the degassing tank and enabling the catalyst stripped to return to the reactor through the regenerator sloped pipe;
wherein the regenerator comprises a reaction section of the regenerator and a disengager section of the regenerator, the disengager section of the regenerator is communicated with the reaction section of the regenerator, an outlet of the reaction section of the regenerator is located inside the disengager section of the regenerator;
a first splitter, a second splitter and a third splitter are arranged in the disengager section of the regenerator, the first splitter and the second splitter are both located above the outlet of the reaction section; the first splitter is a component for reducing a gas velocity in the upward direction of a gas flow discharged from the outlet of the reaction section;
the second splitter comprises a second cover with openings in both upper and lower ends, the second splitter is a cover in a shape of a truncated cone, or the second splitter is a cover in a spherical cap-shaped structure and the spherical cap-shaped structure is provided with an outlet; and the first splitter is located in the second splitter;
the third splitter is located above the second splitter, the third splitter is a third cover with cross-sectional areas gradually decreases from bottom to top, and the third cover has an opening only in a lowermost end, and
a cyclone is arranged in the disengager section and outside of the first splitter, the second splitter and the third splitter, and is not connected with the first splitter, the second splitter or the third splitter.

13. The method according to claim 12, wherein the first splitter is a first cover, a cross-sectional area of the first cover gradually decreases from bottom to top, and the first cover has an opening only in the lowermost end; a minimum distance of a gap between the first splitter and the second splitter is greater than a cross-sectional diameter of the outlet of the reaction section.

14. The method according to claim 12, wherein a cross-sectional area of an end, close to the outlet of the reaction section, of the first splitter is greater than or equal to a cross-sectional area of the outlet of the reaction section.

15. The method according to claim 12, wherein the first splitter comprises a first cover in a conical structure with cross sections gradually increasing from bottom to top, edges of a section of the first cover passing through a cone apex in the longitudinal direction are present by two curves passing through the cone apex, and a curvature of each curve firstly increases and then decreases from the cone apex to the cone base edge; and
the first splitter further comprises a cavity in a conical structure with cross sections gradually increasing from top to bottom; an end, adjacent to the outlet of the reaction section, of the cavity is a base of the cavity; an end, away from the outlet of the reaction section, of the first cover is a base of the first cover, and the base of the first cover is connected with the base of the cavity.

16. The method according to claim 12, wherein the second splitter further comprises a diversion pipe, and an end of the diversion pipe is connected with the opening in the upper end of the second cover.

17. The method according to claim 12, wherein a cross-sectional area of the lowermost end of the third splitter is greater than or equal to the cross-sectional area of the outlet of the second splitter, a cross-sectional area of an annular gap formed between the outlet of the diversion pipe and the third splitter is greater than or equal to a cross-sectional area of the outlet of the diversion pipe;
or, the cross-sectional area of the lowermost end of the third splitter is equal to the cross-sectional area of the outlet of the second splitter.

18. The method according to claim 1,
wherein a temperature of an outlet of the reactor is 700-750° C.

19. The method according to claim 12, wherein a temperature of an outlet of the reactor is 700-750° C.

* * * * *